(12) United States Patent
Corradi

(10) Patent No.: US 8,933,288 B2
(45) Date of Patent: Jan. 13, 2015

(54) SYSTEM AND PROCESS FOR FLUSHING RESIDUAL FLUID FROM TRANSFER LINES IN SIMULATED MOVING BED ADSORPTION

(71) Applicant: UOP LLC, Des Plaines, IL (US)

(72) Inventor: Jason T. Corradi, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/847,832

(22) Filed: Mar. 20, 2013

(65) Prior Publication Data
US 2014/0288345 A1    Sep. 25, 2014

(51) Int. Cl.
C07C 7/12    (2006.01)

(52) U.S. Cl.
CPC .......................................... C07C 7/12 (2013.01)
USPC ............ 585/828; 585/820; 585/829; 585/830

(58) Field of Classification Search
None
See application file for complete search history.

(56) References Cited

U.S. PATENT DOCUMENTS

| | | | |
|---|---|---|---|
| 3,201,491 A | 8/1965 | Stine | |
| 3,455,815 A | 7/1969 | Fickel | |
| 3,715,409 A | 2/1973 | Broughton | |
| 3,732,325 A | 5/1973 | Pharis | |
| 3,761,533 A | 9/1973 | Otani | |
| 4,031,156 A | 6/1977 | Geissler | |
| 5,750,820 A | 5/1998 | Wei | |
| 5,884,777 A | 3/1999 | Pan | |
| 5,912,395 A | 6/1999 | Noe | |
| 6,004,518 A | 12/1999 | Green | |
| 6,149,874 A | 11/2000 | Hotier | |
| 7,208,651 B2 * | 4/2007 | Frey | 585/828 |
| 7,977,526 B2 * | 7/2011 | Porter | 585/828 |
| 8,168,845 B2 * | 5/2012 | Porter et al. | 585/828 |
| 8,329,975 B2 * | 12/2012 | Pieper et al. | 585/820 |
| 8,404,918 B2 * | 3/2013 | Frey | 585/826 |
| 2006/0199989 A1 * | 9/2006 | Frey | 585/828 |
| 2009/0247806 A1 * | 10/2009 | Porter | 585/827 |
| 2012/0152802 A1 * | 6/2012 | Pieper et al. | 208/26 |

OTHER PUBLICATIONS

U.S. Appl. No. 13/630,649, filed Sep. 28, 2012, Jason T. Corradi.
U.S. Appl. No. 13/630,608, filed Sep. 28, 2012, Jason T. Corradi.
U.S. Appl. No. 13/630,447, filed Sep. 28, 2012, James W. Harris.
U.S. Appl. No. 13/630,461, filed Sep. 28, 2012, Jason T. Corradi.
U.S. Appl. No. 13/630,415, filed Sep. 28, 2012, Stanley J. Frey.
U.S. Appl. No. 13/630,428, filed Sep. 28, 2012, Stanley J. Frey.
U.S. Appl. No. 13/630,698, filed Sep. 28, 2012, James W. Harris.

* cited by examiner

Primary Examiner — Tam M Nguyen

(57) ABSTRACT

A process according to various approaches includes flushing an intermediate transfer line between a raffinate stream transfer line and a desorbent stream transfer line away from the adsorptive separation chamber to remove residual fluid including desorbent from intermediate transfer line. The process may include directing the residual fluid flushed from the intermediate transfer line to a recycle stream to introduce the residual fluid into the adsorptive separation chamber.

11 Claims, 5 Drawing Sheets

SYSTEM AND PROCESS FOR FLUSHING RESIDUAL FLUID FROM TRANSFER LINES IN SIMULATED MOVING BED ADSORPTION

FIELD OF THE INVENTION

The subject invention relates to a process for flushing residual fluid from a transfer line in an adsorptive separation process for separating a preferentially adsorbed component from a feed stream. More specifically, the invention relates to a system and process for flushing residual desorbent fluid from a transfer line prior to withdrawing a raffinate stream through the transfer line during the continuous simulated countercurrent adsorptive separation of aromatic hydrocarbons.

BACKGROUND OF THE INVENTION

Para-xylene and meta-xylene are important raw materials in the chemical and fiber industries. Terephthalic acid derived from para-xylene is used to produce polyester fabrics and other articles which are in wide use today. Meta-xylene is a raw material for the manufacture of a number of useful products including insecticides and isophthalic acid. One or a combination of adsorptive separation, crystallization and fractional distillation have been used to obtain these xylene isomers, with adsorptive separation capturing a great majority of the market share of newly constructed plants for the dominant para-xylene isomer.

Processes for adsorptive separation are widely described in the literature. For example, a general description directed to the recovery of para-xylene was presented at page 70 of the September 1970 edition of CHEMICAL ENGINEERING PROGRESS (Vol. 66, No 9). There is a long history of available references describing useful adsorbents and desorbents, mechanical parts of a simulated moving-bed system including rotary valves for distributing liquid flows, the internals of the adsorbent chambers and control systems. The principle of using a simulated moving bed to continuously separate the components of a fluid mixture by contact with a solid adsorbent is as set forth in U.S. Pat. No. 2,985,589. U.S. Pat. No. 3,997,620 applies the principle of the simulated moving bed to the recovery of para-xylene from a feed stream containing $C_8$ aromatics, and U.S. Pat. No. 4,326,092 teaches meta-xylene recovery from a $C_8$-aromatics stream.

Adsorptive separation units processing $C_8$ aromatics generally use a simulated countercurrent movement of the adsorbent and the feed stream. This simulation is performed using established commercial technology wherein the adsorbent is held in place in one or more cylindrical adsorbent chambers and the positions at which the streams involved in the process enter and leave the chambers are slowly shifted along the length of the beds. A typical adsorptive separation unit is illustrated in FIG. 7 and includes at least four streams (feed, desorbent, extract and raffinate) employed in this procedure and the location at which the feed and desorbent streams enter the chamber and the extract and raffinate streams leave the chamber are simultaneously shifted in the same direction at set intervals. Each shift in location of the transfer points delivers or removes liquid to or from a different bed within the chamber. In general, to simulate countercurrent movement of the adsorbent relative to the fluid stream within the chamber, the streams are shifted in the general direction of fluid flow, i.e. the downstream direction, within the chamber to simulate the solid adsorbent moving in the opposite, i.e. upstream, direction. The lines at these transfer points are reused as each stream enters or leaves the associated bed, and each line therefore carries one of the four process streams during some point of the cycle.

The art recognizes that the presence of residual compounds in the transfer lines can have detrimental effects on a simulated-moving-bed process. U.S. Pat. Nos. 3,201,491; 5,750,820; 5,884,777; 6,004,518; and 6,149,874 teach the flushing of the line used to deliver the feed stream to the adsorbent chamber as a means to increase the purity of the recovered extract or sorbate component. Such flushing avoids contamination of the extract stream with raffinate components of the feed remaining in this line when it is subsequently used to withdraw the extract stream from the chamber. U.S. Pat. No. 5,912,395 teaches flushing of the line just used to remove the raffinate stream in order to avoid contaminating feed with raffinate when this line is used to deliver the feed stream to the adsorbent chamber. All of these references teach flushing such lines back into the adsorbent chamber, thus increasing the separation load within the chamber. U.S. Pat. No. 7,208,651 discloses flushing away from the adsorbent chamber the contents of a transfer line which previously has been used to remove the raffinate stream with one or both of a feed mixture and a material withdrawn from the adsorption zone. The residual raffinate within the transfer line is flushed to join the raffinate stream as feed to a raffinate column. U.S. Pat. No. 6,149,874 discloses flushing residual feed from a common section of fluid distribution piping to a booster circuit.

One previous exemplary system s utilized up to three flushes to handle residual fluid remaining in the transfer lines. A primary flush displaced residual extract from the transfer line just used to remove the extract stream with fluid from the desorption zone of the chamber just below the desorbent stream and directed it through a rotary valve to a transfer line just used to inject the feed stream. Because the volumes in the transfer lines were about equal, the extract-plus-desorbent fluid displaced the residual feed that had previously been in the transfer line into the adsorbent chamber just above the current feed stream position so that the residual feed could be separated with the feed stream within the adsorptive separation chamber and to avoid contamination of the extract stream with the residual feed remaining in the transfer line when the extract stream subsequently shifted to the transfer line previously occupied by the feed stream. Further, the residual extract from the primary flush used to displace the feed remained in the transfer line to be subsequently withdrawn by the extract stream to increase yield of the extract product.

The exemplary system sometimes included a secondary flush. The secondary flush utilized a flush of fluid, typically desorbent, through the transfer line and into the chamber immediately below the extract line. The secondary flush provided a "wash" of this transfer line with the desorbent to minimize the amount of contaminates, including raffinate, feed, and other components that may remain in the transfer line after the primary flush so that these materials were not withdrawn from the transfer line with the extract. Because this transfer line was previously flushed with desorbent and extract via the primary flush, the secondary flush was typically used in applications requiring high purity extract. The secondary flush would push the extract and desorbent material previously in the transfer line back into the adsorptive separation chamber. The secondary flush is an optional flush utilized to meet high purity demands of the extract product.

In some systems, a tertiary flush was also utilized. The tertiary flush included a flush of the transfer line previously occupied by the raffinate withdrawal stream. The tertiary flush was utilized to remove the residual raffinate from this transfer line to restrict this raffinate from being injected back into the adsorbent chamber with the feed upon subsequent arrival of the feed stream to the transfer line. Because the raffinate stream is depleted of the desired extract component, the tertiary flush was carried out so that the residual raffinate was not injected back into the adsorptive separation chamber, which would otherwise increase the separation demands in order to remove this additional raffinate material. The tertiary flush was accomplished by flushing the transfer line away from the adsorptive separation chamber with fluid from a port of the chamber adjacent to the transfer line.

SUMMARY OF THE INVENTION

According to various approaches, a process is provided for separating components in a feed stream by simulated countercurrent adsorptive separation. The process includes introducing a feed stream and a desorbent stream into two different ports via two different corresponding transfer lines along a multi-bed adsorptive separation chamber. The feed stream has at least one preferentially adsorbed component and at least one non-preferentially adsorbed component. The multi-bed adsorptive separation chamber has plurality of beds that are serially connected in fluid communication and comprising a predetermined number of spaced ports with corresponding transfer lines in fluid communication therewith for introducing and removing fluid into and from the adsorptive separation chamber. The process also includes withdrawing an extract stream and raffinate stream through two different ports of the multi-bed adsorptive separation chamber via two different corresponding transfer lines. The process according to this approach includes flushing an intermediate transfer line between the first intermediate transfer line and the extract stream transfer line away from the adsorptive separation chamber to remove residual fluid from intermediate transfer line. The process also includes directing the residual fluid flushed from the intermediate transfer line to a recycle stream to introduce the residual fluid into the adsorptive separation chamber. In this manner an amount of fluid required by the process may be reduced.

According to one approach, the process includes transferring residual fluid flushed from the intermediate transfer line to a bottoms portion of a raffinate fractionation column to be sent to the recycle stream. According to another approach, the process includes transferring the residual fluid flushed from the intermediate transfer line a bottoms portion of an extract fractionation column to be sent to the recycle stream. According to these approaches, the residual fluid is not heated to an extract column bottoms outlet temperature thereby reducing energy consumption.

According to another approach, a process is provided for the separation of components in a feed stream comprising at least one preferentially adsorbed component and at least one non-preferentially adsorbed component by simulated countercurrent adsorptive separation that includes introducing a feed stream into a port of a multi-bed adsorbent chamber comprising a plurality of ports with corresponding transfer lines via a transfer line in fluid communication with the port. The process also includes flushing residual feed from the transfer line into the adsorptive separation chamber with a flushing fluid to fill the transfer line with the flushing fluid. The process according to this approach further includes flushing residual flushing fluid in the transfer line away from the adsorptive separation chamber with fluid from a purification zone of the adsorptive separation chamber adjacent to the port to fill the transfer line with the purification zone fluid. The process also includes withdrawing an extract stream from the adsorptive separation chamber through the transfer line that has a higher concentration of the preferentially adsorbed component than the feed stream and a lower concentration of the non-preferentially adsorbed component than the feed stream. In this manner, the transfer line is filled with purification zone fluid having a similar composition to the extract stream prior to withdrawal of the extract stream therethrough to restrict contamination of the extract stream with the non-preferentially adsorbed component.

Figure 1:
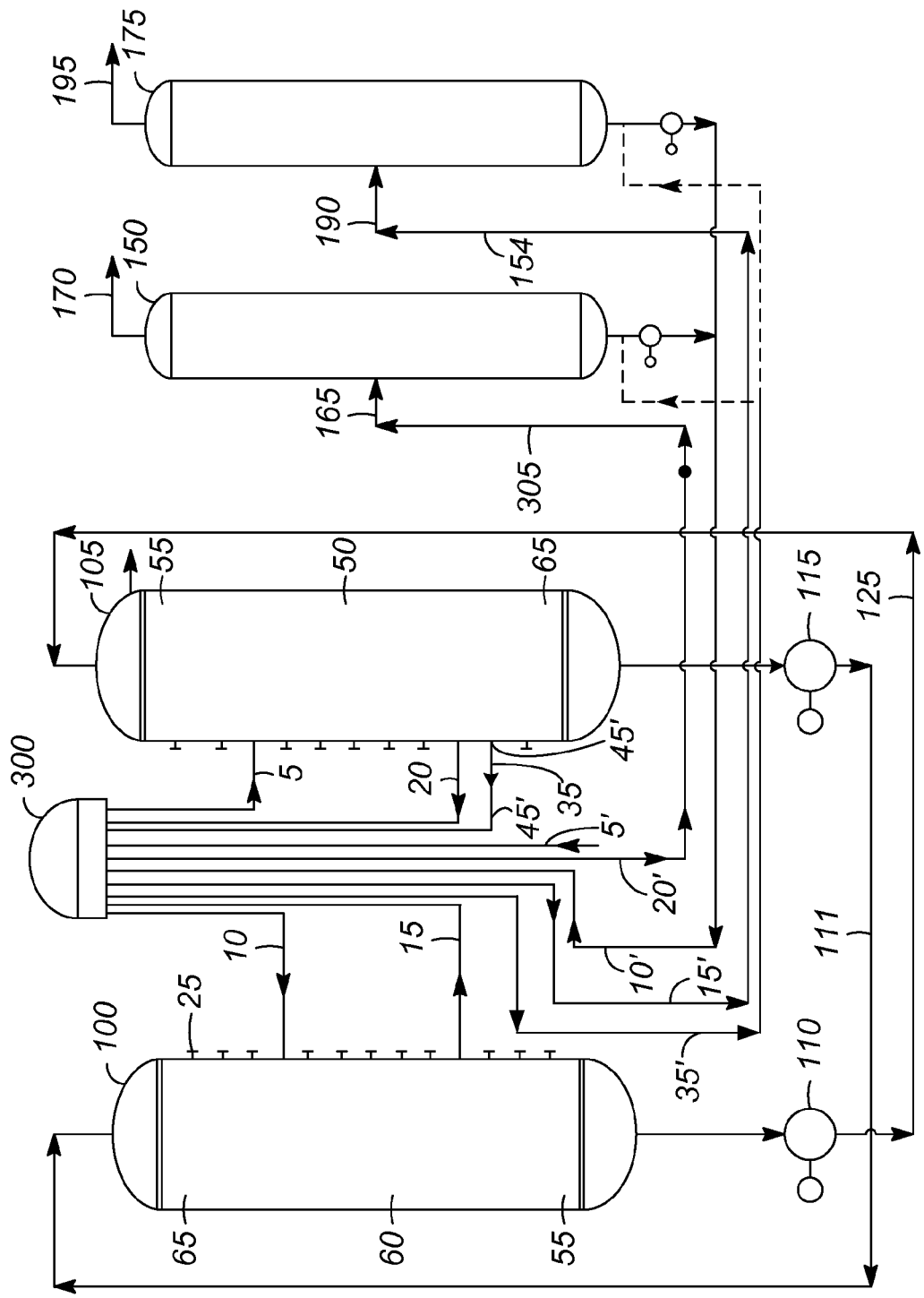
FIG. 1 is a simplified diagram of a simulated-moving-bed adsorption process in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION AND PREFERRED EMBODIMENTS

Co-pending unpublished U.S. patent application Ser. No. 13/630,461 describes a process wherein a first portion of the raffinate stream is directed to a recycle line and a second portion is directed to the raffinate column. As the transfer line used for withdrawing the raffinate stream was previously occupied by the desorbent stream, residual desorbent remains in the transfer line. By directing this first portion of the raffinate stream away from the raffinate column, separation of this residual desorbent in the raffinate column and the associated energy penalty could be avoided. It has been identified, however, that in some systems, when no surge capacity in the feed to the raffinate column is available, the feed to the column may be discontinuous and compromise steady column control.

Adsorptive separation is applied to the recovery of a variety of hydrocarbon and other chemical products. Chemical separations using this approach which have been disclosed include the separation of mixtures of aromatics into specific aromatic isomers, of linear from nonlinear aliphatic and olefinic hydrocarbons, of either paraffins or aromatics from a feed mixture comprising both aromatics and paraffins, of chiral compounds for use in pharmaceuticals and fine chemicals, of oxygenates such as alcohols and ethers, and of carbohydrates such as sugars. Aromatics separations include mixtures of dialkyl-substituted monocyclic aromatics and of dimethyl naphthalenes. A major commercial application, which forms the focus of the prior references and of the following description of the present invention without so limiting it, is the recovery of para-xylene and/or meta-xylene from mixtures of $C_8$ aromatics, due to typically high purity requirements for these products. Such $C_8$ aromatics usually are derived within an aromatics complex by the catalytic reforming of naphtha followed by extraction and fractionation, or by transalkylation or isomerization of aromatics-rich streams in such complexes; the $C_8$ aromatics generally comprise a mixture of xylene isomers and ethylbenzene. Processing of $C_8$ aromatics using simulated-moving-bed adsorption generally is directed to the recovery of high-purity para-xylene or high-purity meta-xylene; high purity usually is defined as at least 99.5 wt.-% of the desired product, and preferably at least 99.7 wt.-%. It should be understood, that while the following detailed description focuses on the recovery of high-purity para-xylene from a mixed xylene and ethylbenzene stream, the invention is not so limited, and is also applicable for separating other components from a stream comprising two or more components. As used herein, the term preferentially adsorbed component refers to a component or components of a feed stream that are more preferentially adsorbed than one or more non-preferentially adsorbed components of the feed stream.

The invention normally is employed in an adsorptive separation process which simulates countercurrent movement of the adsorbent and surrounding liquid as described above, but it may also be practiced in a cocurrent continuous process, like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated herein, for additional description of these adsorption fundamentals. Countercurrent moving-bed or simulated-moving-bed countercurrent flow systems have a much greater separation efficiency for such separations than fixed-bed systems, as adsorption and desorption operations are continuously taking place with a continuous feed stream and continuous production of extract and raffinate. A thorough explanation of simulated-moving-bed processes is given in the Adsorptive Separation section of the Kirk-Othmer ENCYCLOPEDIA OF CHEMICAL TECHNOLOGY at page 563.

Figure 7:
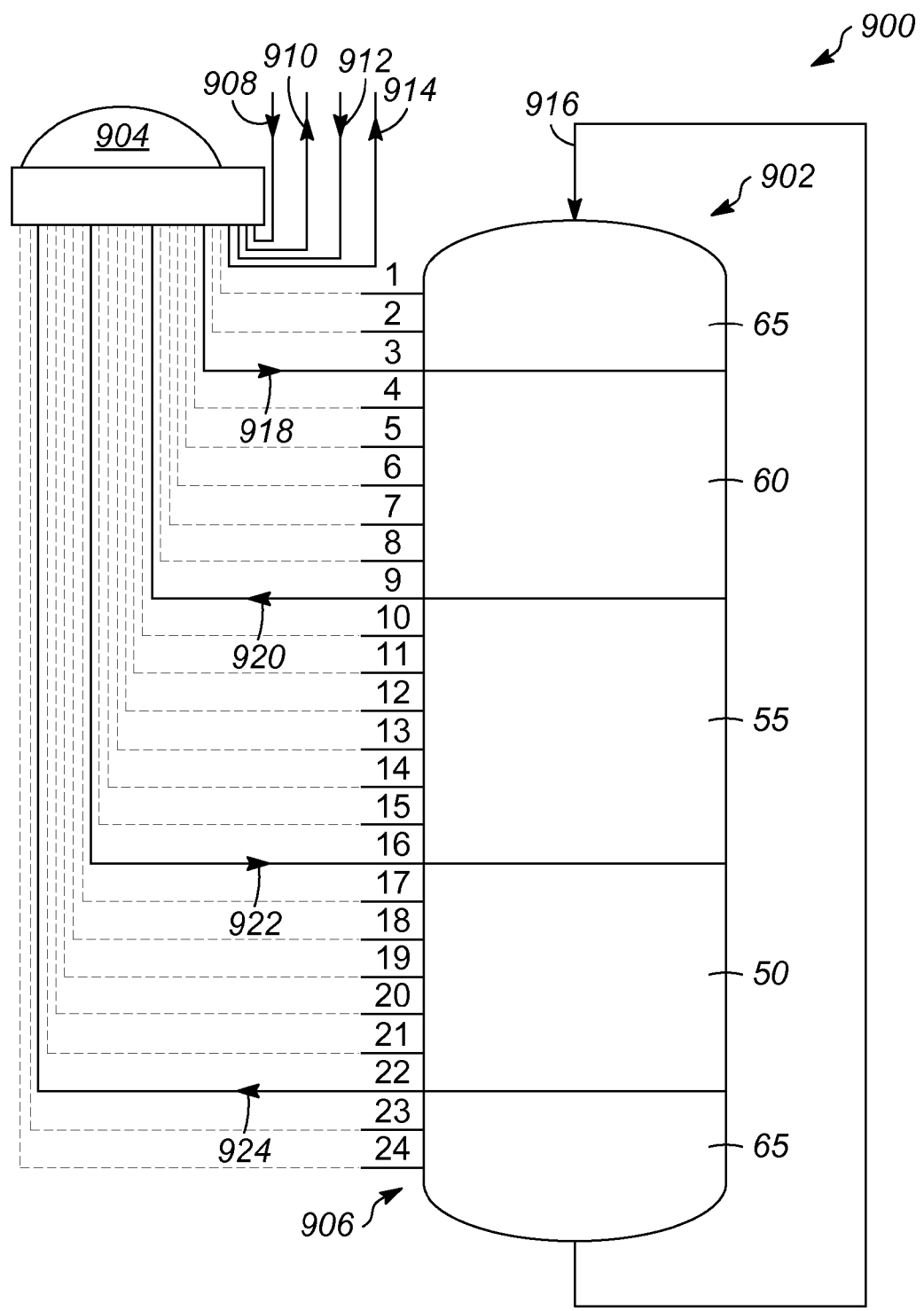
FIG. 7 is a simplified diagram of a Prior Art simulated-moving-bed adsorption process.

FIG. 1 is a schematic diagram of a simulated-moving-bed adsorption process in accordance with one aspect. The process sequentially contacts a feed stream 5 with adsorbent contained in the vessels and a desorbent stream 10 to separate an extract stream 15 and a raffinate stream 20. In the simulated-moving-bed countercurrent flow system, progressive shifting of multiple liquid feed and product access points or ports 25 down an adsorbent chamber 100 and 105 simulate the upward movement of adsorbent contained in the chamber. The adsorbent in a simulated-moving-bed adsorption process is contained in multiple beds in one or more vessels or chambers; two chambers 100 and 105 in series are shown in FIG. 1, although a single chamber 902 as illustrated in FIG. 7 or other numbers of chambers in series may be used. Each vessel 100 and 105 contains multiple beds of adsorbent in processing spaces. Each of the vessels has a number of ports 25 relating to the number of beds of adsorbent, and the position of the feed stream 5, desorbent stream 10, extract stream 15 and raffinate stream 20 are shifted along the ports 25 to simulate a moving adsorbent bed. Circulating liquid comprising desorbent, extract and raffinate circulates through the chambers through pumps 110 and 115, respectively. Systems to control the flow of circulating liquid are described in U.S. Pat. No. 5,595,665, but the particulars of such systems are not essential to the present invention. A rotary disc type valve 300, as characterized for example in U.S. Pat. Nos. 3,040,777 and 3,422,848, effects the shifting of the streams along the adsorbent chamber to simulate countercurrent flow. Although the rotary disc valve 300 is described herein, other systems and apparatus for shifting the streams along the adsorbent chamber are also contemplated herein, including systems utilizing multiple valves to control the flow of the streams to and from the adsorbent chamber 100 and/or 105 as for example, described in U.S. Pat. No. 6,149,874.

Figure 3:
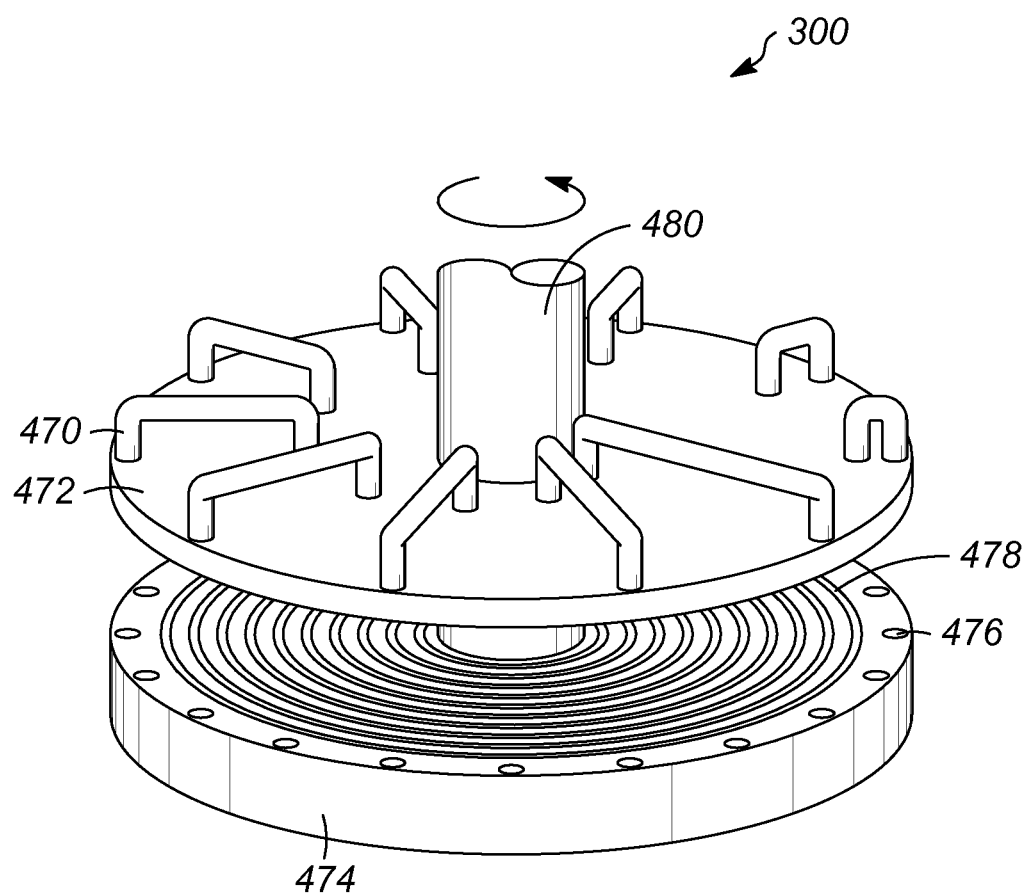
FIG. 3 is a perspective view of a rotary valve in accordance with various embodiments of the invention.

Referring to FIG. 3, a simplified exploded diagram of an exemplary rotary valve 300 for use in an adsorptive separation system and process is depicted. A base plate 474 includes a number of ports 476. The number of ports 476 equal the total number of transfer lines to the chamber(s) 100 and 105. The base plate 474 also includes a number of tracks 478. The number of tracks 478 equal the number of net input, output, and flush lines for the adsorptive separation unit (not shown in FIG. 3, but illustrated as 5', 10', 15', 20', and 35' in FIG. 1). The net inputs, outputs, and flush lines are each in fluid communication with a dedicated track 478. Crossover lines 470 place a given track 478 in fluid communication with a given port 476. In one example, the net inputs include a feed input and a desorbent input, the net outputs include an extract output and a raffinate output, and the flush lines include between about one and about four flush lines. As the rotor 480 rotates as indicated each track 478 is placed in fluid communication with the next successive port 476 by crossover line 470. A seal sheet 472 is also provided. It should be noted that FIG. 3 generically represents a rotary valve of the type that can be used in the present system and process, however it should not be understood that the number of tracklines 478, crossover lines 470, etc., corresponds to the number that would be present in any given system as the specific rotary valve design depends on the total number of net stream to and from the rotary vavle, which may be different, for example, depending upon the line flushing protocol that is utilized and the number of flushing streams that are present.

The various streams involved in simulated-moving-bed adsorption as illustrated in the figures and discussed further below with regard to the various aspects of the invention described herein may be characterized as follows. A "feed stream" is a mixture containing one or more extract components or preferentially adsorbed components and one or more raffinate components or non-preferentially adsorbed components to be separated by the process. The "extract stream" comprises the extract component, usually the desired product, which is more selectively or preferentially adsorbed by the adsorbent. The "raffinate stream" comprises one or more raffinate components which are less selectively adsorbed or non-preferentially adsorbed. "Desorbent" refers to a material capable of desorbing an extract component, which generally is inert to the components of the feed stream and easily separable from both the extract and the raffinate, for example, via distillation.

The extract stream 15 and raffinate stream 20 from the illustrated schemes contain desorbent in concentrations relative to the respective product from the process of between 0% and 100%. The desorbent generally is separated from raffinate and extract components by conventional fractionation in, respectively, raffinate column 150 and extract column 175 as illustrated in FIG. 1 and recycled to a stream 10' by raffinate column bottoms pump 160 and extract column bottoms pump 185 to be returned to the process. FIG. 1 shows the desorbent as bottoms from the respective column, implying that the desorbent is heavier than the extract or raffinate; different commercial units for the separation of $C_8$ aromatics employ either light or heavy desorbents, and thus in some applications the desorbent may be separated at a different location along the fractionation columns 150 and 175. The raffinate product 170 and extract product 195 from the process are recovered from the raffinate stream and the extract stream in the respective columns 150 and 175; the extract product 195 from the separation of $C_8$ aromatics usually comprises principally one or both of para-xylene and meta-xylene, with the raffinate product 170 being principally non-adsorbed $C_8$ aromatics and ethylbenzene.

The liquid streams, e.g., the streams of feed 5, desorbent 10, raffinate 20, and extract 15 entering and leaving the adsorbent chambers 100 and 105 via the active liquid access points or ports 25 effectively divide the adsorbent chamber 100 and 105 into separate zones which move as the streams are shifted along the ports 25. It should be noted that while much of the discussion herein refers to FIG. 1 and the location of the streams in FIG. 1, FIG. 1 illustrates only a current location of the streams at a single step or a snapshot of the process as the streams typically shift downstream at different steps of a cycle. As the streams shift downstream, the fluid composition and the corresponding zones shift downstream therewith. In one approach, the position of the streams with regard to the access points or ports 25 of the adsorptive separation chambers 100 and 105 remain generally constant with regard to one another as they synchronously progress downstream along the ports 25. In one example, the streams each progress a single port 25 downstream for each step and each stream occupies each port 25 one time during an entire cycle. According to one example, the streams are stepped simultaneously to subsequent ports 25 by rotating a rotary valve 300, and are maintained at a particular port 25 or step for a predetermined step-time interval. In one approach, there are between about 4 and 100 ports 25, between about 12 and 48 ports in another approach, and between about 20 and 30 ports in yet another approach, and an equal number of corresponding transfer lines. In one example, the adsorptive separation chamber or chambers 100 and 105 include about 24 ports and each stream is shifted to each of the 24 ports 25 during a complete cycle so that each stream occupies each port 25 and corresponding transfer line during the cycle. In this example, a cycle may be between about 20 and about 40 minutes in one approach and between about 22 and 35 minutes in another approach. In one approach, a step-time interval is between about 30 seconds and about two minutes. In another approach, the step-time interval is between about 45 seconds and about one minute thirty seconds. In yet another approach, the step-time interval is between about 50 seconds and about one minute and 15 seconds. An example of a typical step-time interval may be about 1 minute.

Figure 2:
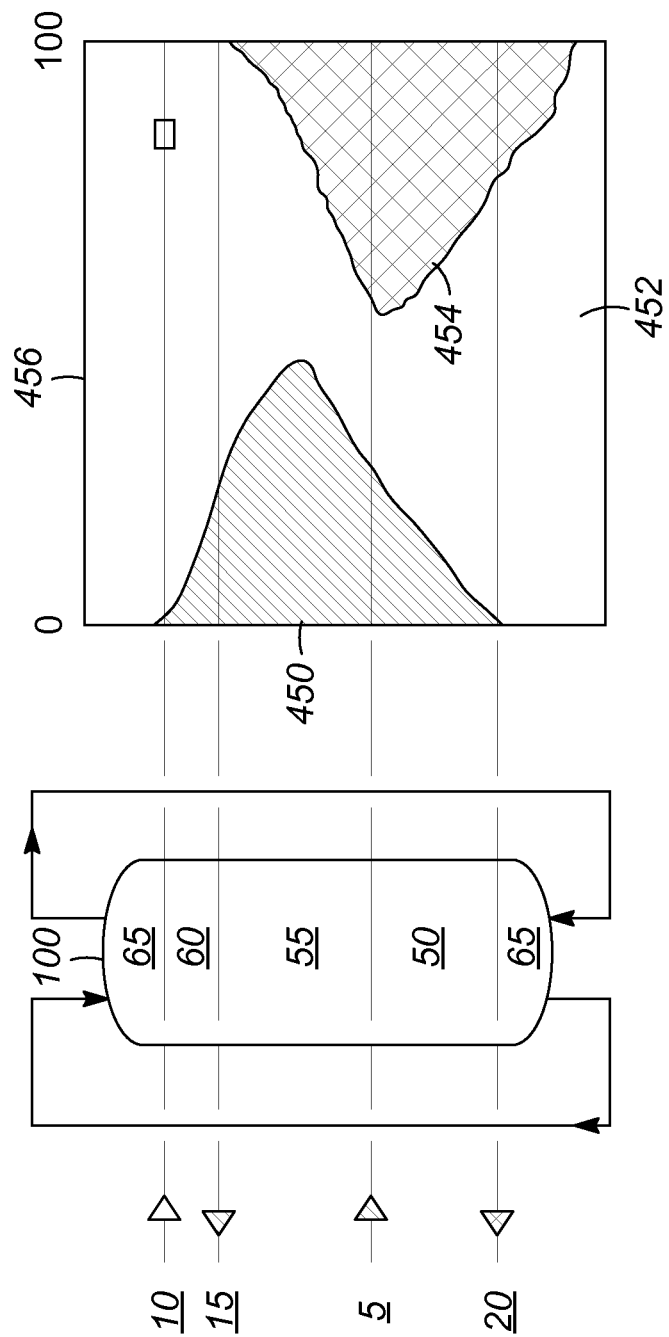
FIG. 2 is a compositional diagram of fluid within a simulated-moving-bed adsorptive separation chamber in accordance with various embodiments of the invention.

With this in mind, FIG. 2 illustrates a snapshot of the compositional profile of the fluid within an adsorptive separation chamber (a single adsorptive separation chamber 100 is illustrated in FIG. 2 for simplicity) at one point during a step and the corresponding zones into which the adsorptive separation chamber 100 is divided. The adsorption zone 50 is located between the feed inlet stream 5 and the raffinate outlet stream 20. In this zone, the feed stream 5 contacts the adsorbent, an extract component is adsorbed, and a raffinate stream 20 is withdrawn. As illustrated in the figure, the raffinate stream 20 may be withdrawn at a location where the composition includes raffinate fluid 454 and little if any extract fluid 450. Immediately upstream with respect to fluid flow is the purification zone 55, defined as the adsorbent between the extract outlet stream 15 and the feed inlet stream 5. In the purification zone 55, the raffinate component is displaced from the nonselective void volume of the adsorbent and desorbed from the pore volume or surface of adsorbent shifting into this zone by passing a portion of extract stream material leaving the desorption zone 60. The desorption zone 60, upstream of the purification zone 55, is defined as the adsorbent between the desorbent stream 10 and the extract stream 15. The desorbent passing into this zone displaces the extract component which was adsorbed by previous contact with feed in the adsorption zone 50. The extract stream 15 may be withdrawn at a location of the chamber 100 that includes extract fluid 450 and little if any raffinate fluid 454. A buffer zone 65 between the raffinate outlet stream 20 and the desorbent inlet stream 10 prevents contamination of the extract, in that a portion of the desorbent stream enters the buffer zone to displace raffinate material present in that zone back into the adsorption zone 50. The buffer zone 65 contains enough adsorbent to prevent raffinate components from passing into the desorption zone 60 and contaminating the extract stream 15.

Each of the zones described above generally are effected through multiple compartments or "beds" as described in U.S. Pat. No. 2,985,589. The positions of the various streams described are structurally separated from one another by a horizontal liquid collection/distribution grid. Each grid is connected to a transfer line defining a transfer point at which process streams enter and leave the adsorbent chamber. This arrangement facilitates the distribution of fluids within the chamber through eliminating channeling and other inefficiencies, prevents convective back-mixing of fluid in a direction opposite to that of primary fluid flow, and prevents migration of adsorbent through the chamber. Each of the zones described above usually comprises a plurality of 2 to 10, and more usually 3 to 8, beds. A typical simulated-moving-bed adsorption unit comprises 24 beds of adsorbent.

It is readily apparent in FIG. 1 that when a transfer line at an access point 25 which is being used to transport a particular stream into or out of the adsorbent chamber is left idle at the end of a step it will remain full of the compounds forming that stream until these compounds are removed from the line by a second flowing stream. In this regard, it should be noted that only active transfer lines, i.e. those lines presently facilitating flow of fluid therethrough, are illustrated in FIG. 1, although intermediate transfer lines are present at each of the ports 25 along the chambers 100 and 105 to facilitate fluid flow upon shifting of the fluid streams to subsequent ports 25. The residual fluid or compounds left in the now unused transfer line after a stream shifts to a subsequent transfer line, will therefore be either withdrawn from the process as the initial part of a process stream removed from the process or forced into the adsorbent chamber when the transfer line carries a stream into the adsorbent chamber. To further understanding, FIG. 7 is included and illustrates a previous system showing unused transfer lines as dashed lines and transfer lines currently occupied by a stream, e.g. stream 920 as solid lines extending from ports of the adsorptive separation chamber 902.

Returning to FIG. 1, as described above, the presence of residual fluid in the transfer lines can have negative effects on the performance of a simulated-moving-bed adsorptive separation process. For example, residual raffinate in a transfer line which previously had been used to remove the raffinate stream 20 from the adsorbent chamber may be flushed into the adsorbent chamber 105 with the feed stream 5 when it shifts to that transfer line in a subsequent step. Similarly, residual feed in a transfer line which previously had been used to introduce the feed stream 5 to the adsorbent chamber may be removed from the transfer line with the extract stream 15 when it shifts to that transfer line in a subsequent step. Likewise, residual extract in a transfer line which previously had been used to remove the extract stream from the adsorbent chamber may be flushed back into the adsorbent chamber 100 with the desorbent stream 10 when it subsequently arrives at that transfer line.

It has been identified that residual fluid, including desorbent remaining in an intermediate transfer line between the transfer line currently occupied by the desorbent stream 10 and the transfer line currently occupied by the raffinate stream 20 after the desorbent stream 10 is stepped to a subsequent transfer line can cause an energy penalty during separation of the raffinate. More particularly, as noted above, when the raffinate stream 20 shifts to the intermediate transfer line and raffinate is withdrawn therethrough, the residual desorbent in the transfer line will be transferred with the raffinate stream 20 along line 20' to the inlet of the raffinate column 150. The desorbent will be heated to the column inlet temperature before being separated from the raffinate product 170 during fractionation. Thus, the residual desorbent is heated to the inlet temperature and cooled back to the original temperature requiring an energy expenditure, without providing a benefit in terms of additional raffinate that is separated, since this residual fluid should have none or very little of the raffinate components in it. Further, it has been identified that the surges of fluid to the column that include very little of the raffinate components, e.g. xylenes, can disturb steady state operation of the column 170.

Turning to FIG. 1, an adsorptive separation system and process in accordance with one aspect is illustrated. According to this aspect, a desorbent flush stream 35 is provided for removing residual fluid from a transfer line that will subsequently be used to withdraw the raffinate stream 20. The desorbent flush stream 35 flushes residual fluid from the transfer line 45 away from the adsorptive separation chamber 105 prior to the withdrawal of the raffinate stream 20 through the transfer line. It should be noted that while the desorbent flush stream 35 is illustrated as removing fluid from the transfer line 45 adjacent to a portion of adsorptive separation chamber 105, during another step of the process the desorbent flush stream 35 will be used to remove residual fluid from a transfer line to adsorptive separation chamber 100. It should also be noted that less than two or more than two adsorptive separation chambers may be utilized within the scope of the description herein.

The desorbent flush stream 35 flushes the residual fluid from the transfer line 45 toward a destination other than the inlet to the raffinate column 150. Advantageously, in this manner, the residual fluid in the transfer line 45 is not mixed with the raffinate stream 20 during withdrawal of the raffinate stream 20 through the transfer line 45 during a subsequent step and sent to the inlet of the raffinate column 150. The first destination may be a recycle line 10' for recycling the raffinate stream and the portion of the residual fluid to the adsorptive separation chamber 100. In this regard, by recycling a portion of the fluid back to the adsorptive separation chamber 100 the amount of fluid processed by the raffinate fractionation column 150 is reduced.

Because the residual fluid in the transfer line will contain a greater percentage of desorbent than the raffinate stream fluid, this excess desorbent is advantageously not sent to and separated in the raffinate fractionation column 150. Because fluid entering the raffinate fractionation column inlet 165 is heated in the column, if the excess desorbent in the residual fluid was introduced into the raffinate fractionation column 150 it would be heated without providing additional yield of the extract product, and thus incurring an energy penalty. Thus, by diverting the initial slug of fluid so that excess desorbent is not introduced into the raffinate fractionation column 150, the amount of energy required by the system is reduced.

Turning to more of the particulars, according to one aspect the desorbent flush stream 35 flushes the residual fluid in the transfer line 45 away from the adsorptive separation chamber 100. It should be noted that the transfer line 45 is used for the desorbent flush stream 35 during the step interval illustrated in FIG. 1, however, during previous or subsequent steps the desorbent flush stream 35 will shift along with the other streams to subsequent transfer lines and be used to remove residual fluid from the subsequent transfer lines.

In one approach, desorbent flush stream 35 is positioned at an intermediate transfer line 45 between desorbent stream 10 and the raffinate stream 20. In this regard, in order to flush the residual fluid from the transfer line 45, fluid from adsorbent chamber 100, and more specifically, the buffer zone 65, adjacent to the transfer line port 45' corresponding to the transfer line 45 is withdrawn from the adsorbent chamber 100 and used to flush the residual fluid away from the adsorbent chamber 100 and 105. The desorbent flush stream 35 may then be transferred for further processing, including recycled to the adsorptive separation chamber via line 10'.

Because this fluid from the buffer zone 65 is similar in composition to the raffinate stream 20 that will be subsequently withdrawn from the transfer line 45, the residual fluid remaining in the bed line after the desorbent flush will advantageously be similar in composition to the desired raffinate stream composition. As there may be several transfer lines in fluid communication with the purification zone between the desorbent stream 10 transfer line and the raffinate stream 20 transfer line, it may be advantageous to flush the residual fluid including the residual desorbent away from an intermediate transfer line using buffer zone fluid that is near the raffinate stream 20 transfer line. In this manner, the buffer zone 65 fluid used to flush the residual fluid from the transfer line 45 may be more similar in composition to the raffinate stream 20 than if the desorbent flush was conducted on a transfer line that was closer to the transfer line currently occupied by the desorbent stream 10. To this end, in one example, the desorbent flush stream 35 is within two transfer lines from the transfer line currently occupied by the raffinate stream 20, and more preferably, by another example, within one transfer line from the transfer line currently occupied by the raffinate stream 20.

In one example, the desorbent stream 10 includes more than about 90% desorbent and in another example more than about 95% desorbent. In one example the desorbent stream 10 includes less than about 10% of the non-preferentially adsorbed components and less than about 1% of the non-preferentially adsorbed components in another example. In one example, the fluid withdrawn from the buffer zone 65 used to flush the residual fluid from the transfer line 45 may include between about 90% and about 95% desorbent and between about 1% and about 5% non-preferentially adsorbed components; and in another example, between about 95% and about 99% desorbent and between about 1% and about 5% non-preferentially adsorbed components.

In one approach, the desorbent flush stream 35 is passed through line 35' to a fluid recycle line 10'. The fluid recycle line 10' may include primarily desorbent that is separated via the fractionation columns 150 and 175 and recycled back to the adsorptive separation chamber 100 where it is reused in the process. In one approach, the desorbent flush stream is sent via line 35' to a bottoms portion 155 of the raffinate fractionation column 150 where it is combined with the desorbent separated by the raffinate fractionation column 150 and sent to the fluid recycle line 10' via a raffinate bottoms pump 160. In another approach the secondary flush stream is sent via line 35' to a bottoms portion 180 of the extract fractionation column 175 where it is combined with the desorbent separated by the extract fractionation column 175 and sent to the fluid recycle line 10' via a extract bottoms pump 185. In yet another approach, first and second portions of the desorbent flush stream may be sent via line 35' to the bottoms portion 155 of the raffinate fractionation column 150 and the bottoms portion 180 of the extract fractionation column 175 respectively.

Further, in one approach, after the desorbent flush of transfer line 45, during a subsequent intermittent step when the raffinate stream 20 is withdrawn through the transfer line 45, fluid within the transfer line 45 will be withdrawn with the raffinate stream 20 and sent to the raffinate fractionation column 150 to be separated via a distillation. The residual fluid within the transfer line 45 after the desorbent flush that is sent with the raffinate stream 20 to the raffinate fractionation column 150 is heated with the raffinate stream 20. Because this residual fluid is more similar in composition to the raffinate stream 20 than the residual fluid previous flushed from transfer line 45, fractionation of this fluid will result in increased recovery of the desired raffinate product 170. Thus, unlike prior systems, fluid remaining in the transfer line 45 after the desorbent flush that is subsequently taken up with the raffinate stream 20 and sent to the raffinate fractionation column 150 will not result in an unnecessary utilities penalty, because distillation of this fluid will result in additional yield of the raffinate product 195 rather than primarily desorbent to be separated out of the column bottoms 155.

In one approach, the desorbent flush stream 35 is withdrawn from the adsorptive separation chamber 100 or 105 and sent along a transfer line 45. In one approach a rotary valve 300 is provided so that the desorbent flush stream 35 is withdrawn through the transfer line 45 and directed to the rotary valve 300. According to this approach, a dedicated desorbent flush stream trackline 478 may be provided, wherein the desorbent flush stream fluid is passed to the desorbent flush net stream line 35'. The residual desorbent net stream flush line 35' may be in fluid communication with the desorbent net line 10' in order to recycle the residual desorbent to the adsorptive separation chambers 100 and 105. To this end, the residual desorbent net stream flush line 35' may be in communication with one or both of the extract column bottoms portion 180 and the raffinate column bottoms portion 155, wherein the residual desorbent can be combined with the bottoms and recycled via line 10' back to the adsorptive separation chambers 100 and 105. Other configurations without a rotary valve 300 are also contemplated herein, such as providing a dedicated residual desorbent flush net stream line for each transfer line of the adsorptive separation chambers 100 and 105.

As described previously, in accordance with various aspects of the invention, countercurrent adsorptive separation includes introducing a feed stream 5, comprising at least one preferentially adsorbed component and at least one non-preferentially adsorbed component, and a desorbent stream 10 into two different ports 25 via two different corresponding transfer lines along a multi-bed adsorptive separation chamber having a plurality of beds that are serially connected in fluid communication and comprising a predetermined number of spaced ports with corresponding transfer lines in fluid communication therewith for introducing and removing fluid into and from the adsorptive separation chamber and withdrawing an extract stream 15 and raffinate stream 20 through two different ports of the multi-bed adsorptive separation chamber via two different corresponding transfer lines. The various streams that are introduced and withdrawn to and from the adsorptive separation chamber 100 and 105 are sequentially shifted or stepped downstream to subsequent ports. The various streams are typically stepped simultaneously to subsequent ports 25, for example by rotating the rotary valve 300, and are maintained at a particular port 25 or step for a predetermined step-time interval. As discussed above, in one approach, there are between about 4 and 100 ports 25, between about 12 and 48 ports in another approach, and between about 20 and 30 ports in yet another approach, and an equal number of corresponding transfer lines. In one example, the adsorptive separation chamber or chambers 100 and 105 include about 24 ports and each stream is shifted to each of the 24 ports 25 during a complete cycle so that each stream occupies each port 25 and corresponding transfer line during the cycle. In this example, a cycle may be between about 20 and about 40 minutes in one approach and between about 22 and 35 minutes in another approach. In one approach, a step-time interval is between about 30 seconds and about two minutes. In another approach, the step-time interval is between about 45 seconds and about one minute thirty seconds. In yet another approach, the step-time interval is between about 50 seconds and about one minute and 15 seconds.

In this regard, the process may include flushing the intermediate transfer line between two lines currently occupied by two of the typical streams, including the feed stream 5, the desorbent stream 10, the extract stream 15, and the raffinate stream 20 at a non-uniform or dynamic volumetric flow rate during the step-time interval. According to one aspect the process includes flushing the intermediate transfer line 45 at a first flow rate during a first portion of the step-time interval. The process includes flushing the intermediate transfer line at a second flow rate during a second portion of the step-time interval later during the step-time interval than the first portion. In this manner, a greater volume of fluid is flushed from the intermediate transfer line during one of the first and second portion of the step-time interval than during the other portion. Flushing the transfer line at a non-constant flow rate may provide performance advantages in terms of the composition of fluid flushed into or from the intermediate transfer line as well as the timing of introducing fluids to or from the intermediate transfer line.

Figure 4:
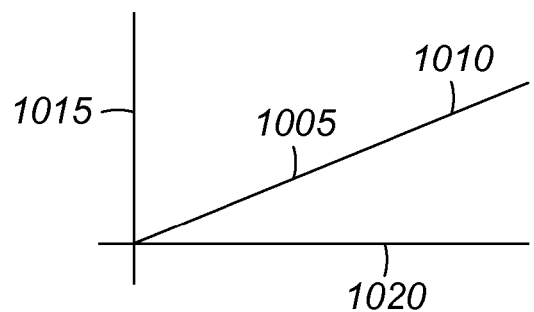
FIGS. 4-6 are graphs illustrating the volumetric flow rate of fluid through transfer lines in accordance with various embodiments of the invention.
Figure 5:
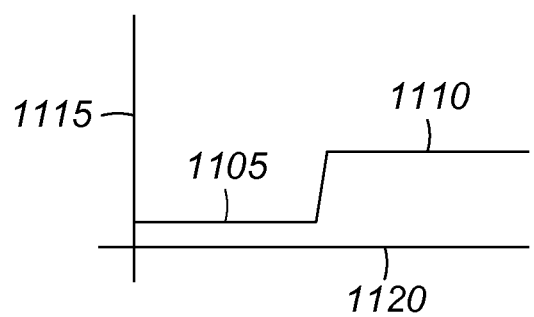
Figure 6:
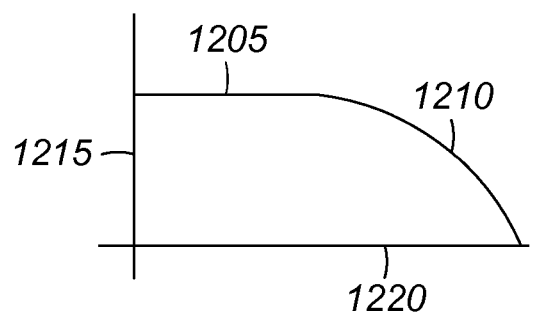

In one aspect, the non-constant flow rate may include a ramped or exponentially increasing or decreasing flow rate that increases or decreases during at least a portion of the step-time interval. In this regard, the ramped flow rate may increase or decrease during a portion of the step-time interval and may vary linearly or non-linearly, e.g. exponentially during that time. By another aspect, the non-constant flow rate may include step increases or decreases in the flow rate so that one or both of the first flow rate and the second flow rate is constant and one is different than the other of the first flow rate and the second flow rate. In yet another aspect, the non-constant flow rate may include a combination of ramped portions and step increases and decreases in the volumetric flow rate. The non-constant flow rate may also include additional flow rates during additional portions of the step-time interval. The flow rate may increase, decrease, or remain unchanged during any particular step. In addition the flow rate may be changed from the initial value to a higher value, lower value or zero at the conclusion of a step. Further one of the flowrates during a step time interval may be a zero flowrate so that little or no fluid flows through the intermediate transfer line during that portion of the step time interval. FIGS. 4-6 illustrate examples of non-constant flow rates in accordance with various aspects. FIG. 4 illustrates a ramped flow rate 1015 that increases over time 1020 during at least a portion of the step-time interval. In this example, a first flow rate 1005 is lower than a second flow rate 1010 so that a greater volume of fluid is flushed during the second portion of the step-time interval than during the first portion. In another example, the ramped flow rate decreases over time so that a first flow rate is higher than a second flow rate so that a greater volume of fluid is flushed during the first portion of the step-time interval than during the second portion. FIG. 5 on the other hand illustrates an example of a non-constant stepped flow rate. In this example, the flow rate 1115 is at a first generally constant flow rate 1105 during a first portion of the step-time interval 1120 and increases to a second and generally constant higher flow rate 1110 during the second portion of the step-time interval 1120. In another example, the stepped flow rate has a second generally constant flow rate during the second portion of the step-time interval that is lower than a first flow rate so that so that more volume of fluid is flushed during the first potion of the step-time interval. The volumetric flow rate during one of the first and second portions may be zero according to various aspects. In yet another example, illustrated in FIG. 6, the flow rate 1215 at a first portion of the step-time interval 1220 begins at a first flow rate 1205 and then includes second flow rate 1210 that exponentially decreases over time during a second portion of the step-time interval 1220. Other flow rate profiles are also contemplated in accordance with various aspects of the invention that have different first and second flow rates during corresponding first and second portions of the step-time interval and may there may be additional portions of the step-time interval with still other flow rates.

In accordance with one aspect, one of the first and second flow rates is sufficient to flush between about 50% and 400% of the volume of the intermediate transfer line 45 and associated valving so that most or all of the residual fluid within the transfer line is flushed during the first or second portion of the step-time interval. According to another aspect, one of the first and second flow rates is sufficient to flush between about 75% and about 200% of the intermediate transfer line 45 and associated valving volume during the first or second portion of the step-time interval. In yet another aspect, one of the first and second flow rates is sufficient to flush between about 90% and about 150% of the intermediate transfer line 45 and associated valving volume during the first or second portion of the step-time interval. The other of the first and second flow rates according to various aspects may be sufficient to flush between about 0% and about 75% of the transfer line and valving volume in one approach, between about 0% and about 50% of the transfer line and valving volume in another approach, and between about 0% and about 25% of the transfer line valving volume in yet another approach.

According to one aspect, the second flow rate is higher than the first flow rate so that a greater volume of fluid is flushed during the second portion of the step-time interval than during the first portion of the step-time interval. The process according to this aspect may be particularly useful where residual fluid is being flushed away from the adsorptive separation chamber 100 and 105 with flushing fluid withdrawn from the adsorptive separation chamber 100 and 105. In this regard, the flushing fluid is provided a greater dwell time within the adsorptive separation chamber than when a constant flow rate is used or when the first flow rate is greater than the second flow rate. This advantageously provides for greater separation of components in the flushing fluid so that the flushing fluid will be more similar in composition than a subsequent stream withdrawn from or introduced into the adsorptive separation chamber 100 and 105.

In one example, the process includes flushing the intermediate transfer line 45, which may include residual desorbent fluid from being previously occupied by the desorbent stream 10, at a first volumetric flow rate during a first portion of the step-time interval that is less than a second volumetric flow rate during a second subsequent portion of the step-time interval. In this manner, as the flushing fluid withdrawn from the buffer zone 65 provided a longer amount of time in the buffer zone 65 so that it is more similar in composition to the raffinate stream 20 that will subsequently be withdrawn from the intermediate transfer line 45 during a subsequent step. By dynamically altering the flowrate of the residual desorbent flush stream 35 in this manner, the residual fluid remaining in the transfer line 45 after the flush will include a smaller amount of desorbent that must be passed to the raffinate column 150, further decreasing the energy penalty associated with separating the raffinate product 170 from the desorbent.

In accordance with various aspects, the volumetric flow rate of the fluid through the transfer lines during dynamic flushing thereof may be controlled using valving and a controller. The valving may be incorporated into transfer lines themselves to control or restrict the volumetric flow rate of fluid flowing therethrough. A controller may be provided for controlling the valves and the flow rate of the fluid through the transfer lines. The valving may also be incorporated in other locations within the system, for example on the downstream side of a rotary valve 300 when a rotary valve is incorporated or in downstream lines for transferring the fluid to downstream components of the system, for example the lines 15' and 20' for transferring fluid to the extract fractionation column 175 or the raffinate fractionation column 150, respectively.

The system described herein for flushing residual fluid may be utilized with one or more additional flush protocols, for example a primary, secondary, or tertiary flush as described previously or one or more of the flush protocols described in Co-pending unpublished U.S. patent application Ser. No. 13/630,461. The flushing protocols may be selected to improve the energy efficiency of the system and process as well as to improve the separation process to meet separation or purity requirements.

A variety of adsorbents may be employed for the present simulated-moving-bed process. The practice of the subject invention thus is not related to or limited to the use of any particular adsorbent or adsorbent/desorbent combination, as differing sieve/desorbent combinations are used for different separations. The adsorbent may or may not include a zeolite. Examples of adsorbents which may be used in the process described herein include nonzeolitic molecular sieves including carbon-based molecular sieves, silicalite and the crystalline aluminosilicates molecular sieves classified as X and Y zeolites. Details on the composition and synthesis of many of these microporous molecular sieves are provided in U.S. Pat. No. 4,793,984, which is incorporated herein for this teaching. Information on adsorbents may also be obtained from U.S. Pat. Nos. 4,385,994; 4,605,492; 4,310,440; and 4,440,871.

In adsorptive separation processes, which generally are operated continuously at relatively constant pressures and temperatures for liquid phase operation, the desorbent material may be selected to satisfy several criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is generally preferred that the adsorbent be more selective for the extract components with respect to a raffinate components than it is for the desorbent material with respect to a raffinate components. Secondly, desorbent materials should be compatible with the particular adsorbent and the particular feed mixture. More specifically, they should not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. The desorbent may include a heavy or light desorbent depending on the particular application. In certain embodiments, a heavy desorbent is selected from the group consisting of para-diethylbenzene, para-diisopropylbenzene, tetralin, and the like, and combinations thereof. In certain embodiments, toluene and the like can be used as the light desorbent. The para-diethylbenzene (p-DEB) has a higher boiling point than the C8 aromatic isomers and, as such, the p-DEB is the bottoms (i.e., heavy) product when separated from the C8 isomers in a fractional distillation column. Similarly, toluene has a lower boiling point than the C8 aromatic isomers and, as such, the toluene is the overhead (i.e., light) product when separated from the C8 isomers in a fractional distillation column. The p-DEB has become a commercial standard for use as a desorbent in separations of para-xylene. Thus, while the above description describes the desorbent as being removed as a bottoms portion of the raffinate and extract fractionation columns, it should be understood that the desorbent may be recovered as overhead or a side cut of the fractionation columns depending on the particular desorbent used and the type of separation.

Adsorption conditions in general include a temperature range of from about 20° to about 250° C., with from about 60° to about 200° C. being preferred for para-xylene separation. Adsorption conditions also include a pressure sufficient to maintain liquid phase, which may be from about atmospheric to 2 MPa. Desorption conditions generally include the same range of temperatures and pressure as used for adsorption conditions. Different conditions may be employed for other extract compounds.

The above description and examples are intended to be illustrative of the invention without limiting its scope. While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

The invention claimed is:

1. A process for separating components in a feed stream by simulated countercurrent adsorptive separation comprising:
   introducing a feed stream, comprising at least one preferentially adsorbed component and at least one non-preferentially adsorbed component, and a desorbent stream into two different ports via two different corresponding transfer lines along a multi-bed adsorptive separation chamber having a plurality of beds that are serially connected in fluid communication and comprising a predetermined number of spaced ports with corresponding transfer lines in fluid communication therewith for introducing and removing fluid into and from the adsorptive separation chamber and withdrawing an extract stream and raffinate stream through two different ports of the multi-bed adsorptive separation chamber via two different corresponding transfer lines;
   flushing residual fluid comprising residual desorbent from an intermediate transfer line between the desorbent stream transfer line and the raffinate stream transfer line away from the adsorptive separation chamber to remove the residual fluid from the intermediate transfer line;
   directing the residual fluid flushed from the intermediate transfer line to a destination other than the inlet of a raffinate column; and
   shifting the raffinate stream to the intermediate transfer line and withdrawing the raffinate stream through the intermediate transfer line.

2. The process of claim 1, wherein flushing the residual fluid includes flushing the residual fluid with buffer zone fluid from the adsorptive separation chamber adjacent to the intermediate transfer line.

3. The process of claim 2, wherein the intermediate transfer line is within two transfer lines of the transfer line currently occupied by the raffinate stream.

4. The process of claim 2, wherein the buffer zone fluid has a lower concentration of desorbent than the residual fluid.

5. The process of claim 2, wherein the raffinate stream is withdrawn along with residual buffer zone material within intermediate the transfer line, and
   passing the raffinate stream and the residual buffer zone material to a raffinate column.

6. The process of claim 1, wherein the one transfer line was previously occupied by the desorbent stream so that the residual fluid within the one transfer line comprises primarily desorbent.

7. The process of claim 6, wherein the residual fluid destination is a desorbent recycle line for recycling desorbent to the desorbent stream to be introduced into the adsorptive separation chamber.

8. The process of claim 1, wherein the feed stream, the desorbent stream, the extract stream, the raffinate stream, and the residual fluid flush stream are sequentially shifted to subsequent ports and their corresponding transfer lines along the predetermined number of spaced ports and corresponding transfer lines and the intermediate transfer line was previously occupied by the desorbent stream before the raffinate stream is withdrawn therethrough so that the residual fluid includes primarily desorbent.

9. The process of claim 8, wherein a rotary valve provides fluid communication between the intermediate transfer line and the recycle line during flushing of the intermediate transfer line, and
   shifting the rotary valve to a subsequent position to remove residual fluid from a subsequent transfer line.

10. The process of claim 9 wherein the rotary valve includes a dedicated residual desorbent flush trackline, and
    passing the residual desorbent stream from the intermediate transfer line, to the residual desorbent flush trackline, and to the destination.

11. The process of claim 1, wherein the flushing the residual fluid from the intermediate transfer line is done during a step time interval and further includes flushing the fluid at a first flowrate during a first portion of the step time interval and flushing the fluid at a second greater flowrate during a second portion of the step time interval.

* * * * *